(12) United States Patent
Berthier et al.

(10) Patent No.: US 8,383,750 B2
(45) Date of Patent: Feb. 26, 2013

(54) AMPHIPHILIC CO-POLYMER CONJUGATES FOR A CONTROLLED RELEASE OF ACTIVE MOLECULES

(75) Inventors: Damien Berthier, Geneva (CH); Lahoussine Ouali, Vetraz-Monthoux (FR); Andreas Herrmann, Veyrier (CH); Daniel Reichlin, Bernex (CH)

(73) Assignee: Firmenich SA, Geneva (CH)

( * ) Notice: Subject to any disclaimer, the term of this patent is extended or adjusted under 35 U.S.C. 154(b) by 513 days.

(21) Appl. No.: 11/916,010

(22) PCT Filed: Jun. 23, 2006

(86) PCT No.: PCT/IB2006/052051
§ 371 (c)(1),
(2), (4) Date: Nov. 29, 2007

(87) PCT Pub. No.: WO2007/007216
PCT Pub. Date: Jan. 18, 2007

(65) Prior Publication Data
US 2008/0279799 A1    Nov. 13, 2008

(30) Foreign Application Priority Data
Jul. 14, 2005    (WO) .................. PCT/IB2005/002006

(51) Int. Cl.
*C08F 18/00* (2006.01)
*A61K 8/02* (2006.01)

(52) U.S. Cl. ........................................ 526/320; 424/401
(58) Field of Classification Search ................... None
See application file for complete search history.

(56) References Cited

U.S. PATENT DOCUMENTS

| | | | |
|---|---|---|---|
| 5,227,272 A | 7/1993 | Kato | |
| 2004/0048754 A1* | 3/2004 | Herrmann et al. | 510/101 |
| 2004/0220074 A1 | 11/2004 | Fehr et al. | 512/1 |

FOREIGN PATENT DOCUMENTS

| EP | 0 432 727 B1 | | 7/1995 |
|---|---|---|---|
| WO | WO 03/049666 | * | 6/2003 |
| WO | WO 03/049666 A2 | | 6/2003 |

OTHER PUBLICATIONS

International Search Report and Written Opinion for PCT/IB2006/052051.

* cited by examiner

*Primary Examiner* — Brian Gulledge
(74) *Attorney, Agent, or Firm* — Winston & Strawn LLP

(57) ABSTRACT

The present invention relates to the field of perfumery. More particularly, it concerns polyethylene or polypropylene based polymers that have at least one β-oxy or β-thio carbonyl moiety capable of liberating a perfuming molecule such as, for example, an α,β-unsaturated ketone, aldehyde or carboxylic ester. The present invention concerns also the use of such compounds in perfumery as well as the perfuming compositions or perfumed articles that include such compounds.

16 Claims, No Drawings

AMPHIPHILIC CO-POLYMER CONJUGATES FOR A CONTROLLED RELEASE OF ACTIVE MOLECULES

TECHNICAL FIELD

The present invention relates to the field of perfumery. More particularly, it concerns amphiphilic co-polymer conjugates based on a polyethylene or polypropylene backbone and comprising at least one β-oxy or β-thio carbonyl moiety capable of liberating an active molecule such as, for example, an α,β-unsaturated ketone, aldehyde or carboxylic ester. The present invention concerns also the use of said co-polymer conjugates in perfumery as well as the perfuming compositions or perfumed articles comprising the invention's compounds.

PRIOR ART

The perfume industry has a particular interest for derivatives which are capable of prolonging the effect of active ingredients over a certain period of time, for example in order to overcome the problems encountered when using perfuming ingredients which are too volatile or have a poor substantivity. In particular, the industry is interested in derivatives capable of performing an improved olfactive performance. Said improvement can be in time, in intensity or in the effective amount of active compound released.

The surface care, in particular skin or textiles, is a particular field in which there is a constant quest to enable the effect such derivatives.

The patent application WO 03/049666 describes a class of compounds capable of prolonging the effect of active ingredients. Amongst these compounds there are mentioned polymers, citing as specific examples a few styrene co-polymers. However, although the performance described in the examples for several monomeric derivatives is quite good, the performance described for the styrene co-polymers is relatively modest (see examples 6 and 7 of the application). There is therefore still a need to improve the release properties of polymer based ingredients capable of prolonging the effect of active ingredients.

The invention's co-polymers are believed to have never been specifically disclosed or suggested in the prior art, nor their particular performances in the field of perfume release.

DESCRIPTION OF THE INVENTION

We have, surprisingly, discovered the existence of particular amphiphilic co-polymer conjugates based on a polyethylene or polypropylene backbone and comprising at least one β-oxy or β-thio carbonyl moiety capable of liberating an active molecule, namely an enone, and having superior performance when compared with the prior art ones. As "active molecule" we mean here any molecule capable of bringing an odor benefit or effect into its surrounding environment, and in particular an odoriferous molecule, i.e. a perfuming ingredient, such as an α,β-unsaturated ketone, aldehyde or carboxylic ester.

Said co-polymer conjugates can be used as perfuming ingredients.

A first object of the present invention concerns co-polymers capable of releasing in a controlled manner active molecules and which are obtainable by a process comprising the co-polymerization of at least one monomer (M) of formula

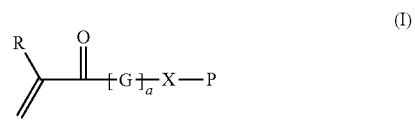

wherein a is 0 or 1;
a) P represents a radical susceptible of generating an odoriferous α,β-unsaturated ketone, aldehyde or carboxylic ester and is represented by formula

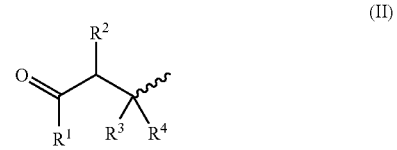

in which the wavy line indicates the location of the bond between said P and X;
$R^1$ represents a hydrogen atom, a $C_1$ to $C_6$ alkoxyl radical or a $C_1$ to $C_{15}$ linear, cyclic or branched alkyl, alkenyl or alkadienyl radical, possibly substituted by $C_1$ to $C_4$ alkyl groups; and
$R^2$, $R^3$ and $R^4$ represent a hydrogen atom, an aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bound together to form a saturated or unsaturated ring having 6 to 20 carbon atoms and including the carbon atom to which said $R^1$, $R^2$, $R^3$ or $R^4$ groups are bound, this ring being possibly substituted by $C_1$ to $C_8$ linear, branched or cyclic alkyl or alkenyl groups;
b) X represents an oxygen or a sulfur atom;
c) R represents a hydrogen atom or a methyl or ethyl group;
d) G represents a group selected from the group consisting of formulae 1) to 4):

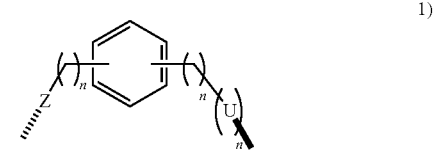

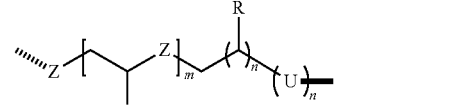

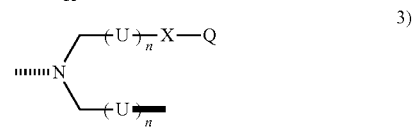

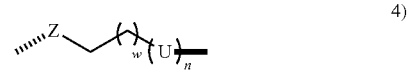

in which formulae the hatched lines indicate the location of the bond between said G and the $CH_2$=CRCO moiety, the bold lines indicate the location of the bond between said G and X; R has the same meaning as above;

m represents an integer varying from 1 to 5;
each n is 0 or 1;
Z represents an oxygen or sulfur atom or a NH or NR$^5$ group, R$^5$ representing a hydrogen atom, a C$_1$-C$_5$ hydrocarbon group or a CH$_2$—U—X-Q or CH$_2$CH$_2$—(U)$_n$—X-Q group;
U is a group of formula —(CO)— or —O(CO)—, the bold line having the same meaning as indicated above;
Q represents a hydrogen atom, an alkali metal atom or a group P as defined above;
w represents an integer from 1 to 20;
and at least a monomer (H) of formula:

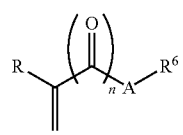
(III)

wherein, R has the meaning given above for formula (I), n is 0 or 1; and
A represents an oxygen or sulfur atom or a NH or NR$^9$ group, R$^9$ representing a hydrogen atom or a C$_1$-C$_5$ hydrocarbon group;
R$^6$ represents:
 if n is 1, a hydrogen atom or an alkali metal atom;
 if n is 0, a COR$^7$ group, R$^7$ being a hydrogen atom or C$_1$-C$_{10}$ group; or
 a C$_1$-C$_{20}$, or a C$_2$-C$_{20}$, hydrocarbon comprising up to four functional groups selected from the group consisting of amine, quaternized nitrogen, COOY and PO$_3$Y, Y being a hydrogen or an alkali metal atom, and optionally comprising one or two functional groups selected from the group consisting of ether and ester.

In the case the monomer of formula (III) is a compound wherein n is 0 and R$^6$ is a COR$^7$ group, and independently of the embodiment of the invention, the process providing the invention's polymer may further comprise a step of hydrolysis so as to transform the AR$^6$ moiety into a OH, SH, NH$_2$ or NHR$^9$ group, e.g. a step wherein the fragment of the copolymers

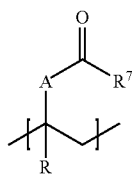

is transformed into the corresponding —[CR(AH)CH$_2$]— moiety.

Furthermore, in the case that the monomer of formula (III) is a compound comprising an acidic/basic function, and independently of the embodiment of the invention, the process providing the invention's polymer may further comprise a step of deprotonation/protonation of said function.

As "odoriferous α,β-unsaturated ketone, aldehyde or carboxylic ester", expression used in the definition of P, we mean here an α,β-unsaturated ketone, aldehyde or carboxylic ester which is recognized by a person skilled in the art as being used in perfumery as perfuming ingredient. In general, said odoriferous α,β-unsaturated ketone, aldehyde or carboxylic ester is a compound having from 8 to 20 carbon atoms, or even more, preferably between 10 and 15 carbon atoms.

Furthermore, according to a particular embodiment of monomer (M), P represents a radical of the formulae (P-1) to (P-11), in the form of any one of its isomers:

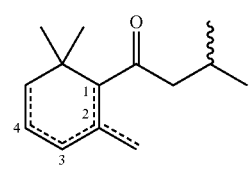
(P-1)

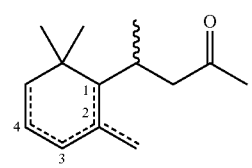
(P-2)

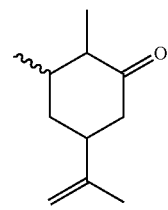
(P-3)

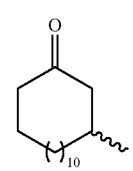
(P-4)

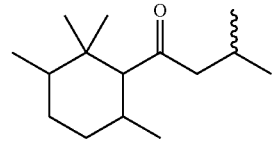
(P-5)

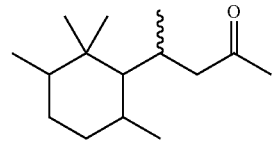
(P-6)

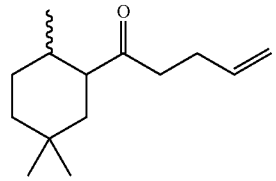
(P-7)

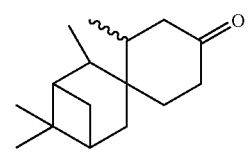
(P-8)

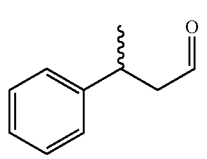
(P-9)

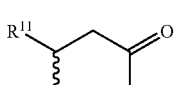
(P-10)

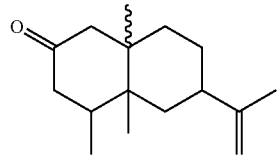
(P-11)

in which formulae the wavy lines have the meaning indicated above and the dotted lines represent a single or double bond, $R^{10}$ indicating a methyl or ethyl group and $R^{11}$ representing a $C_6$ to $C_9$ linear or branched alkyl, alkenyl or alkadienyl group; and with the proviso that at least one of the P groups is of the formulae (P-1) to (P-11) as defined hereinabove.

In particular P may also represent a radical of the formula (P-1) or (P-7) as defined above.

According to a particular embodiment of the monomer (M), G represents a functional group of formula 2) or 4) as defined above.

In particular G may also represent a group of formula 2) wherein Z is an oxygen atom or a NH group, R is hydrogen and n is 0. Alternatively, G may also represent a group of formula 4) wherein w is an integer varying from 1 to 15, and n is 0.

According to another embodiment of the invention, there is used as monomers (M) a compound of the formulae

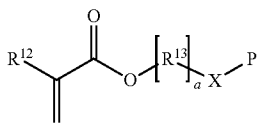
(V)

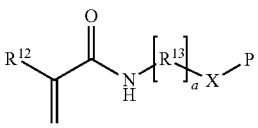
(V')

wherein a, X and P are as defined above;
$R^{12}$ represents a hydrogen atom or a methyl or ethyl group; and
$R^{13}$ represents a group of formula —$[CH_2CH_2O]_k CH_2CH_2$— or —$[CH_2]_j$— wherein k is an integer from 0 to 10, and j is an integer from 2 to 12.

According to a particular embodiment of monomer (H), said monomer is a compound of formula (III) wherein:
R represents a hydrogen atom or a methyl or ethyl group, n is 0 or 1; and
A represents an oxygen or sulfur atom or a NH or $NR^9$ group, $R^9$ representing a hydrogen atom or a $C_1$-$C_3$ hydrocarbon group;

$R^6$ represents:
if n is 1, a hydrogen atom or an alkali metal atom;
if n is 0, a $R^7CO$ group, $R^7$ being a hydrogen atom or $C_1$-$C_5$ group; or
a $C_2$-$C_{15}$ hydrocarbon comprising one or two functional groups selected from the group consisting of amine, quaternized nitrogen, COOY and $PO_3Y$, Y being a hydrogen or an alkali metal atom, and optionally comprising one or two functional groups selected from the group consisting of ether and ester.

According to a particular embodiment of monomer (H), A represents an oxygen or NH or $NR^9$ group, $R^9$ representing a hydrogen atom or a $C_1$-$C_3$ hydrocarbon group.

According to another embodiment of the invention, there is used as monomers (H) a compound of the formulae

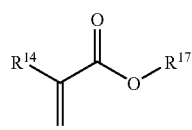
(III¹)

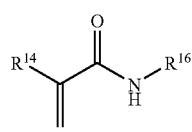
(III²)

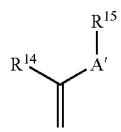
(III³)

wherein $R^{14}$ represents a hydrogen atom or a methyl or ethyl group;
A' is an oxygen atom or a NH group; and
$R^{15}$ represents an acetate or propionate group, a group of formula —$(CH_2)_q$—W, or a group of formula —$(CH_2CH_2O)_x$—$CH_2(CH_2)_x$W, q representing an integer from 2 to 12, x representing an integer from 0 to 2 and W representing a functional group selected from the group consisting of COOY, $NR^{18}_2$ and $NR^{18}_3D$;
$R^{18}$ being a hydrogen atom or a methyl or ethyl group and Y being a hydrogen or an alkali metal atom, D being a monoanion;
$R^{16}$ represents a hydrogen atom or a $R^{15}$; and
$R^{17}$ represents an alkali metal atom or $R^{16}$.

In particular A' may be an oxygen atom or a NH group.
Examples of monoanions are $Cl^-$, $(SO_4^{2-})_{1/2}$, $(HPO_4^{2-})_{1/2}$, $H_2PO_4^-$, or acetate. Examples of alkali metal atoms are sodium or potassium.

The compounds of formula (I), (V) or (V') may be synthesized from commercially available compounds by conventional methods. Generally speaking, the invention's compounds are obtainable by the [1,4]-addition reaction between an odoriferous α,β-unsaturated ketone, aldehyde or carboxylic ester of formula (P')

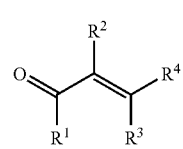
(P')

wherein the configuration of the carbon-carbon double bond can be of the E or Z type and the symbols $R^1$, $R^2$, $R^3$ and $R^4$ have the meaning indicated in formula (I); and a compound of formula $CH_2=CRCO(G)_aXH$, in particular $CH_2=CRCOXH$, wherein all the symbols have the meaning given in formula (I). For practical reasons, and according to the nature and nucleophilicity of the functional group X, the invention compounds may be more advantageously obtained by the reaction between the compound of formula (P'''), which is the aldol derivative of the odoriferous compound of formula (P'),

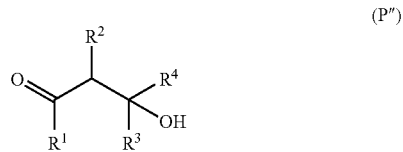

wherein the symbols $R^1$, $R^2$, $R^3$ and $R^4$ have the meaning indicated in formula (I); and an appropriate derivative of $CH_2=CRCO(G)_aXH$, such as for example an acid chloride of formula $CH_2=CRCOCl$ or an anhydride of formula $CH_2=CRCOOCOCR=CH_2$.

The use of the aldol derivative is particularly interesting for the synthesis of all the compounds of formula (I) wherein X represents, e.g., an oxygen atom. On the other hand, the direct use of the odoriferous molecule as starting material is particularly interesting for the synthesis of all the compounds of formula (I) wherein X represents, e.g., a sulfur atom.

General examples of this approach are illustrated in the following scheme, for particular cases of the compounds of formula (I):

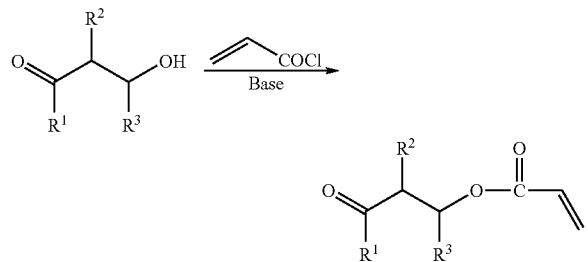

It is not possible to provide an exhaustive list of compounds of formula (P'), which can be used in the synthesis of the invention compounds and subsequently be released. However, the following can be named as preferred examples: alpha-damascone, beta-damascone, gamma-damascone, delta-damascone, alpha-ionone, beta-ionone, gamma-ionone, delta-ionone, beta-damascenone, 3-methyl-5-propyl-2-cyclohexen-1-one, 1(6),8-P-menthadien-2-one, 2,5-dimethyl-5-phenyl-1-hexen-3-one, 1-(5,5-dimethyl-1-cyclohexen-1-yl)-4-penten-1-one, 8 or 10-methyl-alpha-ionone, 2-octenal, 1-(2,2,3,6-tetramethyl-1-cyclohexyl)-2-buten-1-one, 4-(2,2,3,6-tetramethyl-1-cyclohexyl)-3-buten-2-one, 2-cyclopentadecen-1-one, nootkatone, cinnamic aldehyde, 2,6,6-trimethyl-bicyclo[3.1.1]heptane-3-spiro-2'-cyclohexen-4'-one, ethyl 2,4-deca-dienoate, ethyl 2-octenoate, methyl 2-nonenoate, ethyl 2,4-undecadienoate and methyl 5,9-dimethyl-2,4,8-decatrienoate. Of course, the aldol derivatives of formula (P''') of the latter compounds are also useful in the synthesis of the invention compounds.

Amongst the odoriferous compounds cited in the list hereinabove, the preferred ones are: damascones, ionones, beta-damascenone, 1-(5,5-dimethyl-1-cyclohexen-1-yl)-4-penten-1-one, 1(6),8-P-menthadien-2-one, 2-cyclopentadecen-1-one, 1-(2,2,3,6-tetramethyl-1-cyclohexyl)-2-buten-1-one, 4-(2,2,3,6-tetramethyl-1-cyclohexyl)-3-buten-2-one and 2-cyclopentadecen-1-one.

The compounds of formula (III), (III$^1$), (III$^2$) or (III$^3$) are either commercially available or can be synthesized from commercially available compounds by conventional methods.

As mentioned above, the invention's co-polymer conjugates are obtainable by co-polymerization of two types of monomers. Therefore, the invention's co-polymers may be in the form of a random co-polymer or of a block co-polymer. According to a particular embodiment of the invention, the co-polymer is preferentially of the random, or statistic, type.

The co-polymerization process can be promoted by heat, radicals, cations or anions, according to standard methods known for the co-polymerization of acrylate/methacrylate derivatives. However, according to a particular embodiment of the invention, there is used preferably a co-polymerization of the radical type, wherein are reacted together the monomers/blocks. In particular one may cite processes which are promoted by metallocenes or using the ATRP (atom transfer radical polymerization), the RAFT (radical atom fragment polymerization), the MADIX (macromolecular design via interchange of xanthate) or the NMP (nitroxide mediated polymerization) techniques.

Furthermore, according to another embodiment of the invention, the invention's co-polymer conjugates may be characterized by a molecular weight comprised in the range between 500 Da and 1000000 Da, more particularly between 2000 Da and 100000 Da.

Furthermore, it is also useful to mention that the molar ratio between the total amount of monomers (M) and the total amount of monomers (H) (hereinafter (M)/(H)) can be comprised between 1/10 and 10/1, and in particular between 1/6 and 6/1, or even between 1/6 and 1/1.

Owing to their particular chemical structure the invention's co-polymer conjugates are capable of releasing, via a decomposition reaction, a residue and an odoriferous molecule such as, for example, an α,β-unsaturated ketone, aldehyde or carboxylic ester of formula (P').

An example of said decomposition reaction is illustrated in the following scheme:

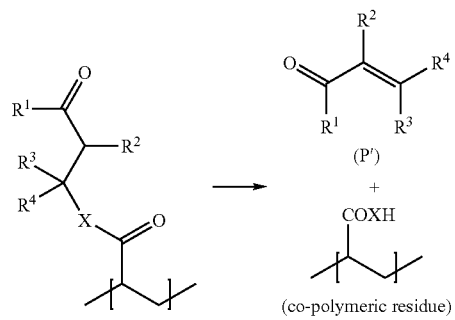

As can be noticed the co-polymers of the invention are composed by at least two types of moieties, a first moiety, generally hydrophobic, of formula $-[CH_2-CR(CO[G]_aXP)]-$, and a second moiety, generally hydrophilic, of formula $-[CH_2-CR(CO)_nAR^6]-$.

According to our tests, the nature of the first moiety is believed to be important for the release of the perfuming ingredient and in particular X plays an important role in the release kinetics of the odoriferous molecule. Thus, by a careful choice of the nature of X it is possible to tune the perfume release properties of the invention's co-polymers.

Furthermore, still according to our tests, the second moiety is believed to play an important role for the pro-fragrance stability and performance by influencing the effective deposition/substantivity of the co-polymer on the surface used for the application, especially on fabrics and hair as well as the release properties of the first moiety. These second moieties can be non ionic, anionic or cationic. For instance, in the case of co-polymers comprising a second moiety bearing essentially carboxylic acids is has been observed, that said second moiety allows also to fine tune the release properties of the invention's co-polymers, and to the contrary of what reported in the prior art (see the table of Example t in WO 03/049666). Moreover, it has also been observed that the use of a acrylate/methacrylate backbone also allows to obtain an improved performance in application, when compared to the prior art polymers, this improved releasing performance being achieved while maintaining a good stability of the pro-fragrance, i.e. the co-polymer conjugates, in the consumer product.

For all types of co-polymers, it is believed that said second moiety influences also the releasing properties of the invention's co-polymer by allowing changes of the spatial structure of the latter as a function of the polymer's environment.

The decomposition reaction, which leads to the release of the odoriferous molecules, is believed to be influenced by pH changes or by heat, but may also be triggered by other types of mechanisms.

As mentioned above, the invention concerns the use of the above-described co-polymers as perfuming ingredients. In other words it concerns a method to confer, enhance, improve or modify the odor properties of a perfuming composition or of a perfumed article, which method comprises adding to said composition or article an effective amount of at least a co-polymer according to the invention. By "use of an invention's co-polymer" it has to be understood here also the use of any composition containing said co-polymers and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's co-polymers as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient.

Said perfuming co-ingredient is not a co-polymer according to the invention. Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability and etc. A detailed description of the nature and type of adjuvant commonly used in perfuming bases cannot be exhaustive, but it has to be mentioned that said ingredients are well known to a person skilled in the art.

An invention's composition consisting of at least one co-polymer and at least one perfumery carrier represents a particular embodiment of the invention as well as a perfuming composition comprising at least one co-polymer, at least one perfumery carrier, at least one perfumery base, and optionally at least one perfumery adjuvant.

It is useful to mention here that the possibility to have, in the compositions mentioned above, more than one of the invention's co-polymers or other delivery systems of similar type is important as it enables the perfumer to prepare accords, perfumes, possessing the odor tonality of various compounds of the invention, creating thus new tools for their work.

Furthermore, an invention's co-polymer, or a perfuming composition comprising it, is a useful perfuming ingredient, which can be advantageously used in all the fields of modern perfumery, such as fine perfumery or functional perfumery. Indeed, the invention compounds may be advantageously employed in fine or functional perfumery to achieve a more controlled deposition, and consequent release, of odoriferous compounds. For example, the co-polymers according to the invention, owing to a good substantivity, a low volatility and a well controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin. Consequently, a perfumed article comprising:

i) as perfuming ingredient, at least one invention's co-polymer as defined above; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's co-polymer.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or anti-perspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention co-polymer, so that it may be necessary to protect the latter from premature decomposition, for example by encapsulation.

Preferred perfuming compositions or perfumed articles are perfumes, fabric detergents or softener bases.

Typical examples of fabric detergents or softener composition into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The above-mentioned consumer product bases are all characterized by being practically neutral (e.g. body care products or perfumes), acidic (e.g. fabric softeners) or basic (e.g. detergents, soaps), while the amphiphilic co-polymers of the inventions, can be either non-ionic or ionic (cationic or anionic).

We have found that, according to a particular embodiment of the invention, when the consumer product bases have a pH value above 8, (such as detergents or soaps) then it is preferable to combine such a base with an invention's co-polymer having an increased positive charge at acidic or neutral pH as compared to basic pH, i.e. co-polymers comprising amino groups.

Similarly, we have found that, according to a particular embodiment of the invention, when the consumer product bases have a pH value below 6, (such as softeners) then it is preferable to combine such a base with an invention's co-polymer having an increased negative charge at basic or neutral pH as compared to acidic pH, i.e. a co-polymer comprising COOY groups.

Furthermore, still according to a particular embodiment of the invention, polymers having charges that are independent of the pH (in the range between 3 and 12), i.e. polymers comprising $PO_3Y$ groups or quaternized nitrogen atoms, can be used at the entire range of pH values encountered in different consumer products.

The proportions in which the co-polymers according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the co-polymers of the invention based on the weight of the composition into which they are incorporated. Concentrations lower than these, such as in the order of 0.01% to 5% by weight, can be used when these co-polymer are applied directly in the perfuming of the various consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's co-polymer. Suitable surfaces are, in particular, textiles, hard surfaces, hair and skin.

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacement $\delta$ are indicated in ppm with respect to the TMS as standard, the coupling constants J are expressed in Hz.

Commercially available reagents and solvents were used without further purification, if not stated otherwise. Reactions were carried out in standard glassware under $N_2$ or Ar and yields are not optimized. Demineralized water was obtained from a Millipore Synergy 185 water purifier. Column chromatography (CC): Silica gel 60 Å (35-70 microns from SDS). IR Spectra: Perkin Elmer 1600 or Spectrum One FTIR spectrometer, $\nu$ in $cm^{-1}$. GC-MS (EI): HP 5890 or 6890 GC System equipped with a Supelco SPB-1 capillary column (30 m, 0.25 mm i.d.) at 70° for 10 min then to 260° (10°/min), helium flow ca. 1 ml/min, coupled with a HP MSD 5972 or 5973 quadrupole mass spectrometer, electron energy ca. 70 eV, fragment ions m/z (rel. int. in % of the base peak).

Analytical Size Exclusion Chromatography (SEC). SEC analyses were performed at room temperature (ca. 22° C.) on a system composed of a ThermoFinnigan Surveyor vacuum online degasser, quaternary LC pump, autosampler and UV/Vis detector combined with a ThermoSeparationProducts (tsp) Spectra System IR-150 refractometer and a Viscotek 270 Dual Detector viscometer. Samples were eluted from a Macherey-Nagel Nucleogel GPC 104-5 column (300× 7.7 mm i.d., particle size 5 µm) at a flow rate of 1.0 ml/min using HPLC grade THF from SDS. Universal calibrations were carried out with the viscometer and the RI detector using commercial polystyrene (PS) or poly(methyl methacrylate) (PMMA) polymer standards from Fluka. About 40 mg of the polymer standards were precisely weighed and dissolved in 10 ml of solvent, then 50 µl of these solutions were injected for the calibration.

Example 1

Preparation of the Polymers Bearing Carboxylic Groups According to the Invention Preparation of the Monomer:

(±)-1-Methyl-3-oxo-3-(trans-2,6,6-trimethyl-3-cyclohexen-1-yl)propyl 2-Methacrylate (1)

A solution of freshly distilled methacrylic acid (2.87 g, 33.3 mmol), 4-dimethylaminopyridine (DMAP, 3.25 g, 26.6 mmol) and (±)-trans-3-hydroxy-1-(2,6,6-trimethyl-3-cyclohexen-1-yl)-1-butanone (7.00 g, 33.3 mmol) in $CH_2Cl_2$ (35 ml) was cooled to 0° C. before a solution of N,N'-dicyclohexyl carbodiimide (DCC, 7.54 g, 36.6 mmol) in $CH_2Cl_2$ (15 ml) was added dropwise during 20 min. The reaction mixture was stirred at room temperature for 5 d. The precipitate formed in the reaction was filtered off and the filtrate taken up in $CH_2Cl_2$, washed with HCl (10%, 2×), a saturated solution of $Na_2CO_3$ (2×) and a saturated solution of NaCl (2x, pH≈7). The organic layer was dried ($Na_2SO_4$) and concentrated. Repetitive column chromatography ($SiO_2$, heptane/ether 9:1) gave 4.67 g (63%) of a slightly yellow oil.

IR (neat): 3017w, 2956m, 2929m, 2872m, 2829w, 1709s, 1652w, 1636m, 1451m, 1399m, 1375s, 1352m, 1317s, 1296s, 1266w, 1250w, 1225w, 1211w, 1164s, 1136s, 1115m, 1077m, 1062m, 1030s, 1008m, 998m, 987w, 937s, 911m, 900w, 885w, 862m, 848m, 813m, 787m, 752m, 699s, 682s.

$^1$H-NMR: 6.06-6.02 (m, 1H); 5.58-5.49 (m, 2H); 5.48-5.35 (m, 2H); 3.05 and 2.89 (dd, J=17.9, 6.7, 1H); 2.71 and 2.54 (dd, J=17.9, 6.1, 1H); 2.58-2.46 (m, 1H); 2.29-2.21 (m, 1H); 2.02-1.93 (m, 1H); 1.92 (m, 3H); 1.75-1.66 (m, 1H); 1.32 (d (2×), J=6.1, 3H); 1.02 and 0.99 (s, 3H); 0.95 and 0.93 (s, 3H); 0.89 and 0.88 (d, J=7.2 and 6.7, 3H).

$^{13}$C-NMR: 211.50 (s); 211.20 (s); 166.55 (s); 136.63 (s); 136.60 (s); 131.80 (d); 131.73 (d); 125.15 (t); 125.10 (t); 124.19 (d); 124.13 (d); 67.03 (d); 66.79 (d); 63.04 (d); 62.87 (d); 53.21 (t); 41.75 (t); 41.71 (t); 33.12 (s); 33.09 (s); 31.63 (d); 31.53 (d); 29.75 (q); 20.69 (q); 19.96 (q); 19.93 (q); 19.84 (q); 18.34 (q); 18.31 (q).

MS (EI): 193 (6), 192 (40), 177 (7), 155 (5), 149 (3), 135 (5), 124 (5), 123 (34), 122 (24), 121 (5), 109 (4), 108 (8), 107 (31), 95 (5), 93 (5), 91 (7), 87 (3), 83 (5), 82 (3), 81 (17), 79 (6), 77 (4), 70 (5), 69 (100), 67 (6), 55 (5), 53 (3), 43 (7), 42 (3), 41 (21), 39 (6).

Preparation of the Protected Co-Polymers:

Random Co-polymer of (±)-1-Methyl-3-oxo-3-(trans-2,6,6-trimethyl-3-cyclohexen-1-yl)propyl 2-Methacrylate and tert-Butyl Methacrylate (ca. 1:5) (2a)

tert-Butyl methacrylate (0.90 g, 6.3 mmol) and 1 (0.35 g, 1.3 mmol) were solubilized in dry anisole (4 ml) before 2,2'-azobisisobutyronitrile (AIBN, 12.4 mg, 0.08 mmol) was added under $N_2$. The medium was degassed with two freeze-pump-thaw cycles and heated at 90° C. for 6 h. The polymer was then solubilized in THF and precipitated into cold methanol (twice) to give 0.95 g (76%) of a white solid.

IR (neat): 2975w, 2933w, 2873w, 2830w, 1717w, 1474w, 1457w, 1391w, 1366m, 1248m, 1133w, 1029w, 967w, 874w, 846m, 751w, 699w, 682w, 667w.

$^1$H-NMR: 5.53 (m, 1H); 5.45 (m, 1H); 5.10 (m, 1H); 3.06 (m, 1H); 2.86 (m, 1H); 2.72 (m, 1H); 2.50 (m, 3H); 2.36 (m, 1H); 2.30-1.65 (m, 16H); 1.42 (m, 45H); 1.31 (m, 6H); 1.20-0.74 (m, 25H).

$^{13}$C-NMR: 211.32 (s, br.); 177.47 (s, br.); 176.66 (s, br.); 131.73 (d, br.); 124.28 (d, br.); 80.91 (s, br.); 80.82 (s, br.); 67.84 (d, br.); 63.05 (d, br.); 52.89 (t, br.); 46.23 (s, br.); 45.34 (s, br.); 41.72 (t); 33.05 (s, br.); 31.65 (d, br.); 29.76 (q, br.); 27.81 (d); 20.73 (q, br.); 19.89 (q, br.); 19.62 (q, br.); 17.82 (q, br.); 17.63 (q, br.).

Average molecular weight (SEC, PMMA): $M_w$=47000 Da, $M_n$=18000 Da.

Random Co-polymer of (±)-1-Methyl-3-oxo-3-(trans-2,6,6-trimethyl-3-cyclohexen-1-yl)propyl 2-Methacrylate and tert-Butyl Methacrylate (ca. 1:3) (2b)

As described for 2a with 0.33 ml of tert-butyl methacrylate (2.0 mmol), 0.19 g of 1 (0.7 mmol) in dry anisole (3.1 ml) and 4.4 mg of AIBN (0.03 mmol) to give 0.32 g (63%) of a white solid.

IR (neat): 2972m, 2931m, 2876m, 2830w, 1718s, 1474m, 1458m, 1390m, 1365s, 1247m, 1133s, 1063m, 1030m, 998w, 968w, 941w, 875w, 846s, 784w, 750m, 699m, 682m.

$^1$H-NMR: 5.53 (m, 1H); 5.46 (m, 1H); 5.10 (m, 1H); 3.05 (m, 1H); 2.86 (m, 1H); 2.72 (m, 1H); 2.50 (m, 2H); 2.21 (m, 2H); 2.12-1.63 (m, 8H); 1.43 (m, 27H); 1.28 (m, 4H); 1.20-0.69 (m, 20H).

$^{13}$C-NMR: 211.62 (s, br.); 176.65 (s, br.); 131.79 (d, br.); 124.33 (d, br.); 80.96 (s, br.); 80.61 (s, br.); 67.87 (d, br.); 62.73 (d, br.); 52.88 (t, br.); 46.24 (s, br.); 45.35 (s, br.); 41.70 (t); 33.10 (s, br.); 31.68 (d, br.); 29.79 (q, br.); 27.81 (d); 20.71 (q, br.); 19.88 (q, br.); 19.64 (q, br.); 17.91 (q, br.).

Average molecular weight (SEC, PMMA): $M_w$=35800 Da, $M_n$=16100 Da.

Random Co-polymer of (±)-1-Methyl-3-oxo-3-(trans-2,6,6-trimethyl-3-cyclohexen-1-yl)propyl 2-Methacrylate and tert-Butyl Methacrylate (ca. 1:2) (2c)

As described for 2a with 0.41 ml of tert-butyl methacrylate (2.5 mmol), 0.35 g of 1 (1.3 mmol) in dry anisole (6 ml) and 6.2 mg of AIBN (0.04 mmol) to give 0.36 g (52%) of a white solid.

IR (neat): 2972m, 2930m, 2874m, 2828w, 1716s, 1653w, 1637w, 1456m, 1390m, 1366s, 1247s, 1133m, 1063m, 1030m, 998w, 969w, 939w, 847s, 751m, 700m, 682m.

$^1$H-NMR: 5.53 (m, 1H); 5.46 (m, 1H); 5.10 (m, 1H); 3.05 (m, 1H); 2.84 (m, 1H); 2.72 (m, 1H); 2.50 (m, 2H); 2.21 (m, 2H); 2.12-1.63 (m, 6H); 1.43 (m, 18H); 1.28 (m, 6H); 1.20-0.75 (m, 18H).

$^{13}$C-NMR: 211.23 (s, br.); 177.18 (s, br.); 131.70 (d, br.); 124.31 (d, br.); 81.02 (s, br.); 80.58 (s, br.); 67.88 (d, br.); 62.73 (d, br.); 52.89 (t, br.); 46.23 (s, br.); 45.35 (s, br.); 41.70 (t); 33.10 (s, br.); 31.71 (d, br.); 29.77 (q, br.); 27.81 (d); 20.72 (q, br.); 19.89 (q, br.); 19.66 (q, br.); 17.62 (q, br.).

Average molecular weight (SEC, PMMA): $M_w$=54100 Da, $M_n$=26100 Da.

Random Co-polymer of (±)-1-Methyl-3-oxo-3-(trans-2,6,6-trimethyl-3-cyclohexen-1-yl)propyl 2-Methacrylate and tert-Butyl Methacrylate (ca. 1:1) (2d)

As described for 2a with 0.88 ml of tert-butyl methacrylate (5.40 mmol), 1.50 g of 1 (5.4 mmol) in dry anisole (20 ml) and 17.8 mg of AIBN (0.1 mmol) to give 1.60 g (71%) of a white solid.

IR (neat): 3013w, 2957m, 2932m, 2876w, 2830w, 1714s, 1654w, 1601w, 1456m, 1391m, 1366s, 1248s, 1133s, 1062w, 1029w, 966w, 941w, 847m, 784w, 751m, 699m, 682m.

$^1$H-NMR: 5.56 (m, 1H); 5.45 (m, 1H); 5.10 (m, 1H); 3.06 (m, 1H); 2.86 (m, 1H); 2.72 (m, 1H); 2.50 (m, 3H); 2.21 (m, 2H); 2.10-1.60 (m, 6H); 1.42 (m, 9H); 1.26 (m, 6H); 1.20-0.80 (m, 12H).

$^{13}$C-NMR: 211.29 (s, br.); 176.98 (s, br.); 131.69 (d, br.); 124.30 (d, br.); 81.05 (s, br.); 67.91 (d, br.); 62.72 (d, br.); 52.89 (t, br.); 46.10 (s, br.); 45.36 (s, br.); 41.70 (t); 33.10 (s, br.); 31.63 (d, br.); 29.77 (q, br.); 27.83 (d); 20.76 (q, br.); 19.89 (q, br.); 19.62 (q, br.).

Average molecular weight (SEC, PMMA): $M_w$=56900 Da, $M_n$=24600 Da.

Preparation of the Invention's Co-Polymers:

Random Co-polymer of (±)-1-Methyl-3-oxo-3-(trans-2,6,6-trimethyl-3-cyclohexen-1-yl)propyl 2-Methacrylate and Methacrylic Acid (ca. 1:5) (3a)

Trifluoroacetic acid (TFA, 15 ml) was added to a solution of 2a (0.90 g, 0.91 mmol) in $CH_2Cl_2$ (15 ml) and the reaction mixture was stirred at room temperature for 1 h. The medium became orange. Precipitation into cold diethyl ether gave 0.55 g (86%) of a white solid.

IR (neat): 3700-2400w (br.), 2982m, 2969m, 2956m, 2935m, 2900m, 2838m, 1697s, 1474m, 1449m, 1387m, 1369m, 1252m, 1151s, 1065m, 1029w, 999w, 961m, 933m, 832w, 793w, 750w, 700w, 683w, 668w, 632w, 625w, 617w, 605w.

$^1$H-NMR (MeOD): 5.58 (m, 1H); 5.49 (m, 1H); 5.11 (m, 1H); 3.14 (m, 1H); 2.90 (m, 1H); 2.67 (m, 1H); 2.50 (m, 1H); 2.32 (m, 1H); 2.20-1.78 (m, 19H); 1.75 (m, 2H); 1.52 (m, 2H); 1.45 (m, 4H); 1.30 (m, 7H); 1.11-0.73 (m, 32H).

$^{13}$C-NMR (MeOD): 213.50 (s, br.); 183.69 (s, br.); 182.53 (s, br.); 182.24 (s, br.); 181.34 (s, br.); 179.15 (s, br.); 132.81 (d, br.); 125.50 (d, br.); 69.33 (d, br.); 64.03 (d, br.); 55.69 (t, br.); 54.18 (t, br.); 53.20 (t, br.); 52.90 (t, br.); 47.53 (s, br.); 46.32 (s, br.); 45.94 (s, br.); 42.81 (t); 34.19 (s, br.); 32.92 (d, br.); 30.51 (q, br.); 28.24 (q, br.); 21.50 (q, br.); 20.33 (q, br.); 19.93 (q, br.); 19.28 (q, br.); 30.51 (q, br.); 17.36 (q, br.); 17.02 (q, br.).

Random Co-polymer of (1)-1-Methyl-3-oxo-3-(trans-2,6,6-trimethyl-3-cyclohexen-1-yl)propyl 2-Methacrylate and Methacrylic Acid (ca. 1:3) (3b)

As described for 3a with 0.25 g of 2b (0.4 mmol), $CH_2Cl_2$ (5 ml) and TFA (5 ml) to give 0.12 g (63%) of a white solid.

IR (neat): 3696-2182m, 3205m, 3013m, 2977m, 2953m, 2932m, 2881m, 2587m, 1719s, 1694s, 1654m, 1469m, 1449m, 1385m, 1368m, 1249m, 1153s, 1030m, 998w, 932m, 832m, 789m, 755m, 700m, 682m.

$^1$H-NMR (MeOD): 5.58 (m, 1H); 5.49 (m, 1H); 5.11 (m, 1H); 3.14 (m, 1H); 2.90 (m, 1H); 2.67 (m, 1H); 2.50 (m, 1H); 2.32 (m, 1H); 2.20-1.78 (m, 10H); 1.75 (m, 1H); 1.52 (m, 1H); 1.30 (m, 5H); 1.11-0.73 (m, 18H).

$^{13}$C-NMR (MeOD): 213.70 (s, br.); 182.52 (s, br.); 182.24 (s, br.); 181.34 (s, br.); 132.76 (d, br.); 125.51 (d, br.); 69.33 (d, br.); 64.02 (d, br.); 55.74 (t, br.); 54.12 (t, br.); 46.96 (q, br.); 46.74 (q, br.); 46.33 (q, br.); 45.94 (q, br.); 42.84 (t, br.); 34.16 (s, br.); 33.05 (d, br.); 32.92 (d, br.); 30.53 (q, br.); 30.23 (q, br.); 21.37 (q, br.); 20.36 (q, br.); 19.94 (q, br.); 19.25 (q, br.); 17.99 (q, br.); 17.39 (q, br.); 17.02 (q, br.).

Random Co-polymer of (±)-1-Methyl-3-oxo-3-(trans-2,6,6-trimethyl-3-cyclohexen-1-yl)propyl 2-Methacrylate and Methacrylic Acid (ca. 1:2) (3c)

As described for 3a with 0.30 g of 2c (0.5 mmol), $CH_2Cl_2$ (5 ml) and TFA (5 ml) to give 0.17 g (71%) of a white solid.

IR (neat): 3701-2324s (br.), 2954s, 2932s, 2872s, 2830m, 1717s, 1696s, 1452s, 1368s, 1248s, 1136s, 1065s, 1031s, 998m, 963s, 935s, 834s, 792s, 755s, 700s, 682s.

$^1$H-NMR (MeOD): 5.58 (m, 1H); 5.49 (m, 1H); 5.11 (m, 1H); 3.16 (m, 1H); 2.90 (m, 1H); 2.66 (m, 1H); 2.50 (m, 1H); 2.33 (m, 1H); 2.26-1.80 (m, 7H); 1.74 (m, 1H); 1.46 (m, 1H); 1.30 (m, 4H); 1.12-0.86 (m, 15H).

$^{13}$C-NMR (MeOD): 182.20 (s, br.); 181.27 (s, br.); 169.39 (s, br.); 132.76 (d, br.); 125.51 (d, br.); 69.28 (d, br.); 64.03 (d, br.); 63.89 (d, br.); 55.68 (t, br.); 54.08 (t, br.); 46.72 (s, br.); 46.31 (s, br.); 45.92 (s, br.); 42.83 (t, br.); 34.17 (s, br.); 33.08 (d, br.); 32.91 (d, br.); 30.53 (q, br.); 21.49 (q, br.); 20.56 (q, br.); 20.40 (q, br.); 19.97 (q, br.).

Random Co-polymer of (±)-1-Methyl-3-oxo-3-(trans-2,6,6-trimethyl-3-cyclohexen-1-yl)propyl 2-Methacrylate and Methacrylic Acid (ca. 1:1) (3d)

As described for 3a with 0.15 g of 2d (0.4 mmol), $CH_2Cl_2$ (5 ml) and TFA (5 ml) to give 0.10 g (77%) of a white solid.

IR (neat): 3666-2385m (br.), 3013m, 2956s, 2932s, 2876s, 2830m, 1722s, 1700s, 1654m, 1459m, 1448m, 1374s, 1248s, 1135s, 1062s, 1029s, 936s, 840m, 789m, 749m, 700m, 682m.

$^1$H-NMR (MeOD): 5.60 (m, 1H); 5.51 (m, 1H); 5.11 (m, 1H); 3.15 (m, 1H); 2.90 (m, 1H); 2.77 (m, 1H); 2.51 (m, 2H); 2.34 (m, 2H); 2.26-1.63 (m, 8H); 1.31 (m, 4H); 1.23-0.77 (m, 9H).

$^{13}$C-NMR (MeOD): 213.42 (s, br.); 185.10 (s, br.); 181.69 (s, br.); 174.45 (s, br.); 132.78 (d, br.); 125.55 (d, br.); 69.40 (d, br.); 64.00 (d, br.); 54.06 (t, br.); 46.49 (s, br.); 46.34 (s, br.); 45.91 (s, br.); 42.81 (t, br.); 34.21 (s, br.); 32.98 (t, br.); 30.54 (q, br.); 21.57 (q, br.); 20.44 (q, br.); 20.06 (q, br.); 17.33 (q, br.); 17.09 (q, br.).

Co-polymers 3b-d were alternatively prepared in one step by adding AIBN (47.4 mg, 0.29 mmol) under $N_2$ to a solution of 1 (2.00 g, 7.2 mmol) and the corresponding stoichiometric equivalent of methacrylic acid in dioxane (30-40 ml). The medium was degassed with two freeze-pump-thaw cycles and heated at 90° C. for 4 hours. The polymer was then precipitated into cold heptane (twice) to give a white solid. The spectral analyses correspond to those mentioned above.

Example 2

Preparation of the Polymers Bearing Amine Groups According to the Invention

Random Co-polymer of (±)-1-Methyl-3-oxo-3-(trans-2,6,6-trimethyl-3-cyclohexen-1-yl)propyl 2-Methacrylate and 2-(N,N-dimethylamino)ethyl Methacrylate (ca. 1:1) (4a)

AIBN (35.54 mg, 0.216 mmol) was added under $N_2$ to a solution of 2-(N,N-dimethylamino)ethyl methacrylate (1.80 ml, 10.82 mmol) and 1 (3.53 g, 10.82 mmol) in distilled anisole (50 ml). The mixture was degassed by two freeze-pump-thaw cycles and heated to 90° C. for 6 h. The polymer was dissolved in THF and precipitated into in cold heptanes (two times) to give a white solid.

IR (neat): 2955m, 2888m, 2823w, 2770w, 1805w, 1724s, 1653w, 1601w, 1456m, 1376m, 1248m, 1143s, 1100m, 1063m, 1017w, 964m, 898w, 883w, 851w, 752m, 700m, 683m.

$^1$H-NMR: 5.54 (m, 1H); 5.46 (m, 1H); 5.11 (m, 1H); 4.07 (m, 2H); 3.04 (m, 1H); 2.58 (m, 2H); 2.50 (m, 3H); 2.29 (m, 6H); 2.10-1.60 (m, 6H); 1.27 (m, 6H); 1.25-0.60 (m, 16H).

$^{13}$C-NMR: 211.37 (s); 176.50 (s); 131.65 (d); 124.30 (d); 67.89 (d); 62.98 (d); 57.06 (t); 52.99 (t); 45.74 (q); 45.10 (q); 41.70 (t); 33.06 (s); 31.62 (d); 29.76 (q); 21.49 (q); 20.76 (q); 19.88 (q); 16.79 (q).

Average molecular weight (SEC, PMMA): $M_w$=87000 Da, $M_n$=7300 Da.

Random Co-polymer of (±)-1-Methyl-3-oxo-3-(trans-2,6,6-trimethyl-3-cyclohexen-1-yl)propyl 2-Methacrylate and 2-(N,N,N-trimethylamino)ethyl Methacrylate sulfate (ca. 1:1) (4b)

A solution of dimethylsulfate (0.66 ml, 6.90 mmol) in THF (10 ml) was added under $N_2$ to 4a (2.50 g, 5.74 mmol) was solubilized in distilled THF (25 ml). The mixture was stirred at room temperature for 2 h. The quaternized co-polymer precipitated and was filtered and dried under vacuum to give 2.90 g (90%) of a white solid.

IR (neat): 3013w, 2957m, 2932m, 2887w, 2831w, 1803w, 1722s, 1653w, 1625w, 1478m, 1377m, 1225s, 1143s, 1043s, 1010s, 952m, 842m, 748mv700w, 683w.

$^1$H-NMR: 5.58 (m, 1H); 5.49 (m, 1H); 5.15 (m, 1H); 4.48 (m, 2H); 3.85 (m, 2H); 3.71 (s, 1H); 3.34 (m, 12H); 2.92 (m, 1H); 2.48 (m, 1H); 2.35 (m, 1H); 2.24-1.55 (m, 5H); 1.71 (m, 2H); 1.50-0.70 (m, 32H).

$^{13}$C-NMR: 213.32 (s); 177.78 (s); 132.73 (d); 125.52 (d); 69.29 (d); 65.62 (t); 63.71 (d); 59.95 (t); 54.77 (q); 54.09 (q); 46.66 (t); 44.61 (s); 42.83 (t); 34.22 (s); 32.97 (d); 30.57 (q); 23.76 (q); 21.68 (q); 20.39 (q).

Random Co-polymer of (±)-1-Methyl-3-oxo-3-(trans-2,6,6-trimethyl-3-cyclohexen-1-yl)propyl 2-Methacrylate and 2-(N,N-dimethylamino)ethyl Methacrylate (ca. 1:3) (4c)

As described for 4a with 3.60 ml of 2-(N,N-dimethylamino)ethyl methacrylate (21.65 mmol), 2.35 g of 1 (7.22 mmol) and 47.4 mg of AIBN (0.288 mmol) in dry anisole (40 ml) for 7 h to give 5.50 g (96%) of a white solid.

IR (neat): 3013w, 2948m, 2892w, 2870w, 2820m, 2769m, 1805w, 1723s, 1659w, 1625w, 1455m, 1385m, 1376m, 1367m, 1332w, 1263m, 1250m, 1237m, 1143s, 1099m, 1061m, 1041m, 1015m, 963m, 881w, 850m, 778wv749m, 700m, 683m.

$^1$H-NMR: 5.54 (m, 1H); 5.46 (m, 1H); 5.11 (m, 1H); 4.06 (m, 6H); 2.57 (m, 6H); 2.28 (m, 18H); 2.10-1.60 (m, 11H); 1.27 (m, 6H); 1.20-0.75 (m, 24H).

$^{13}$C-NMR: 211.43 (s); 177.36 (s); 176.68 (s); 131.66 (d); 124.29 (d); 67.92 (d); 63.03 (t); 57.10 (t); 54.26 (t); 52.91 (t); 45.81 (q); 44.81 (q); 41.71 (t); 33.07 (s); 31.66 (q); 29.77 (q); 20.75 (q); 19.88 (q); 19.67 (q); 18.91 (q); 16.92 (q).

Random Co-polymer of (±)-1-Methyl-3-oxo-3-(trans-2,6,6-trimethyl-3-cyclohexen-1-yl)propyl 2-Methacrylate and 2-(N,N,N-trimethylamino)ethyl Methacrylate sulfate (ca. 1:3) (4d)

As described for 4b with 2.00 g of 4c (2.67 mmol) in dry THF (40 ml) and 0.91 ml of dimethylsulfate (9.61 mmol) in dry THF (10 ml) to give 2.50 g (83%) of a white solid.

IR (neat): 3476w, 3036w, 2950m, 2834w, 1802w, 1724s, 1651w, 1480m, 1384m, 1217s, 1142s, 1058s, 1004s, 951s, 894m, 869m, 736s, 683w, 609m.

$^1$H-NMR: 5.58 (m, 1H); 5.50 (m, 1H); 5.14 (m, 1H); 4.47 (m, 6H); 3.85 (m, 6H); 3.71 (s, 9H); 3.33 (m, 27H); 2.92 (m, 1H); 2.70 (m, 1H); 2.46 (m, 1H); 2.36 (m, 1H); 2.24-1.55 (m, 14H); 1.50-0.70 (m, 32H).

$^{13}$C-NMR: 205.14 (s); 178.30 (s); 132.79 (d); 125.55 (d); 68.90 (d); 65.52 (t); 63.84 (d); 60.44 (t); 54.72 (q); 46.62 (d); 42.62 (t); 34.23 (s); 32.92 (d); 30.49 (q); 20.91 (q); 20.37 (q).

Random Co-polymer of (±)-1-Methyl-3-oxo-3-(trans-2,6,6-trimethyl-3-cyclohexen-1-yl)propyl 2-Methacrylate and 2-(N,N-dimethylamino)ethyl Methacrylate (ca. 1:5) (4e)

As described for 4a with 6.00 ml of 2-(N,N-dimethylamino)ethyl methacrylate (36.05 mmol), 2.35 g of 1 (7.22 mmol) and 71.04 mg of AIBN (0.43 mmol) in dry anisole (80 ml) for 7 h to give 5.24 g (68%) of a white solid.

IR (neat): 2946m, 2870w, 2821m, 2769m, 1806w, 1722s, 1655w, 1626w, 1455m, 1386m, 1367m, 1332w, 1264m, 1237m, 1143s, 1099m, 1060m, 1041m, 1015m, 959m, 849m, 778m, 749m, 701m, 683m, 608w.

$^1$H-NMR: 5.53 (m, 1H); 5.47 (m, 1H); 5.12 (m, 1H); 4.06 (m, 11H); 2.57 (m, 12H); 2.28 (m, 36H); 2.10-1.60 (m, 16H); 1.27 (m, 6H); 1.17-0.60 (m, 32H).

$^{13}$C-NMR: 195.53 (s); 177.68 (s); 177.28 (s); 176.41 (s); 131.70 (d); 124.27 (d); 63.04 (t); 57.11 (t); 54.30 (t); 52.25 (t); 45.81 (q); 45.08 (q); 44.76 (q); 41.72 (t); 33.07 (s); 31.66 (s); 29.78 (q); 20.74 (q); 19.87 (q); 18.56 (q); 16.84 (q).

Average molecular weight (SEC, PMMA): $M_w$=73000 Da, $M_n$=15600 Da.

Random Co-polymer of (±)-1-Methyl-3-oxo-3-(trans-2,6,6-trimethyl-3-cyclohexen-1-yl)propyl 2-Methacrylate and 2-(N,N,N-trimethylamino)ethyl Methacrylate sulfate (ca. 1:5) (4f)

As described for 4b with 3.32 g of 4e (3.12 mmol) in dry THF (60 ml) and 1.78 ml of dimethylsulfate (18.73 mmol) to give 4.92 g (93%) of a white solid.

IR (neat): 3460w, 3035m, 2953w, 2834w, 1803w, 1724s, 1655w, 1479m, 1385m, 1216s, 1146s, 1057m, 1045m, 1004s, 951m, 894w, 838m, 740s, 683w, 609m.

$^1$H-NMR: 5.58 (m, 1H); 5.49 (m, 1H); 5.14 (m, 1H); 4.48 (m, 9H); 3.89 (m, 10H); 3.71 (s, 14H); 3.34 (m, 69H); 2.46 (m, 1H); 2.36 (m, 1H); 2.22-1.55 (m, 10H); 1.73 (m, 1H); 1.50-0.70 (m, 51H).

$^{13}$C-NMR: 178.31 (s); 132.67 (d); 121.28 (d); 65.44 (t); 60.52 (t); 55.28 (q); 54.72 (q); 46.61 (s); 42.67 (t); 34.24 (s); 33.06 (d); 30.51 (q); 23.75 (q); 19.27 (q).

Example 3

Release of a Perfuming Ingredient from the Invention's Polymers Incorporated into a Consumer Product (Softener)

The polymers described in WO 03/049666 (amphiphilic random co-polymers, based on a styrenic backbone) were compared to the invention's polymers (amphiphilic polymethacrylate) obtained under the same conditions. The polymers which are compared have the same ratio between monomer (M) and monomer (H), formally resulting in the same amount of perfuming ingredient P' in the softener base. The tests were carried out using a standard fabric softener base, generally used to treat terry towels.

The fabric softener base with the following final composition has been prepared:

| Ingredient | Part by weight |
|---|---|
| Stepantex ® VK 90 (origin: Stepan) | 16.7% |
| Calcium chloride solution (10%) | 0.2% |
| Dye | 0.3% |
| Deionized water | 82.8% |

The washing of the terry towels was carried out with 85 g of an un-perfumed detergent base, followed by a rinsing cycle using 35 g of a standard un-perfumed softener. To the above described softener base were previously added 0.5 mmol of pure δ-damascone or, alternatively, the corresponding molar amount of δ-damascone containing polymer.

A washing machine (Miele novotronic W300-33CH) was loaded with 17 small terry towels (18 cm*18 cm, about 30 g each) and 2.3 kg of large cotton towels (10 towels of 50*100 cm). The load was washed at 40° C. using a short cycle program and a rinsed at 900 rpm.

At the end of the washing, the 17 small terry towels were line-dried for 24 h, before being evaluated in intensity and assessment by 20 panelists after 1, 3 and 7 d, using a scale ranging from "1" (no odor) to "7" (very strong).

The results obtained for the different polymers are summarized in Table 1:

TABLE 1

Performance of softeners containing the free perfuming ingredient, the invention's polymer or the polymers according to WO 03/049666.

| Tested molecule | Average intensity[1] |
|---|---|
| 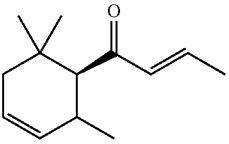<br>δ-damascone (reference) | 2.66 |
| 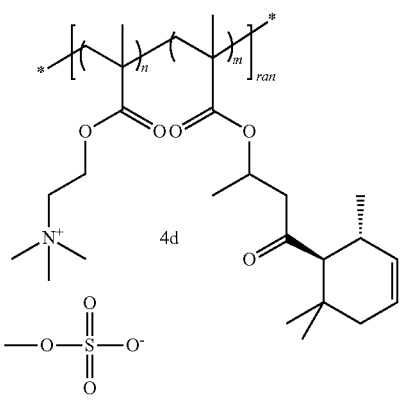<br>prior art compound WO 03/049666: Example 6: compound b) or d) | 2.72 |
| 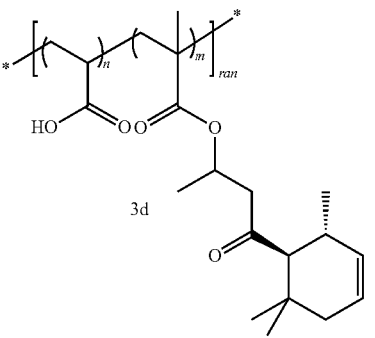<br>4d | 4.35 |
| 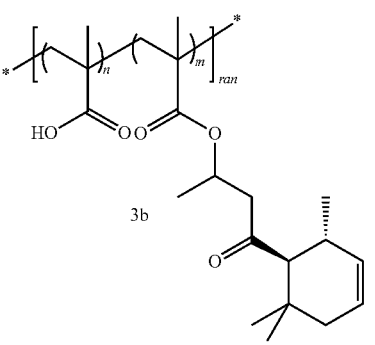<br>3d | 3.27 |
| 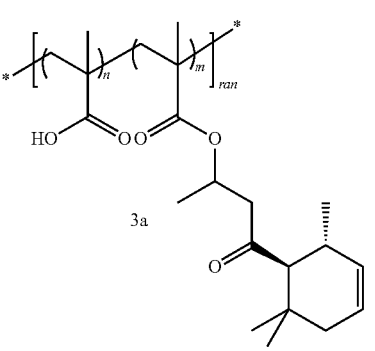<br>3b | 3.68 |
| 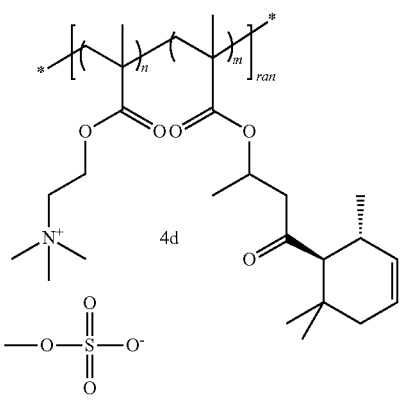<br>3a | 3.55 |

[1] average of the odor intensity of the dry fabric three days after the washing.

As can be noticed from Table 1, the invention's co-polymers always perform better than the free perfuming ingredient or the prior art co-polymer.

Example 4

Release of a Perfuming Ingredient from the Invention's Polymers Incorporated into a Consumer Product (Shampoo)

The polymer was solubilized in water and then added to a standard un-perfumed shampoo base at a concentration corresponding to 0.3% (w/w) of δ-damascone.

The shampoo base with the following final composition has been prepared:

| Ingredient | Part by weight |
| --- | --- |
| Texapon ® NSO IS, sodium laureth sulfate (origin: Henkel) | 40.00% |
| Dehyton ® AB-30, coco-betaine (origin: Henkel) | 4.00% |
| Amphotensid GB 2009, disodium cocoamphodiacetate (origin: Zschimmer & Schwarz) | 3.00% |
| Dow Corning 2-1691 Emulsion (origin: Dow Corning) | 1.00% |
| Rewomid IPP 240, cocamide MIPA (origin: Witco Surfactants) | 1.00% |
| Cetyl alcohol | 1.00% |
| Citric acid solution (20%) | 0.70% |
| Arlypon ® F, laureth-2 (origin: Henkel) | 0.50% |
| Cithrol EGDS 3432, ethylene glycol distearate (origin: Croda) | 0.50% |
| Opacifier 631 (origin: Morton) | 0.50% |
| Lanette ® E, sodium cetearyl sulfate (origin: Henkel) | 0.40% |
| Jaguar Excel, guar hydroxypropyltrimmonium chloride (origin: Rhodia) | 0.20% |
| Tylose H10, hydroxyethylcellulose (origin: Clariant) | 0.20% |
| Glydant ® DMDM hydantoin (origin: Lonza) | 0.15% |
| Phenonip ® (origin: Nipa) | 0.05% |
| Deionized water | 46.80% |

The shampoo base was stirred slowly to obtain a homogenous medium. The test needs 20 g of decontaminated hair swatches. They were hand-rinsed for 30 s with warm water (about 37° C.). The swatches were washed with 5 g of the shampoo base during 30 s with gentle rubbing, and then rinsed for 30 s with warm water. The same swatches are washed a second time with 5 g of the shampoo base.

Nine panelists then evaluated the foam. The swatches were rinsed with cold water for 30 s. The swatches were evaluated 24 h later. To evaluate the intensity of δ-damascone from the swatches, a scale ranging from "1" (no odor) to "7" (very strong) was used. The intensity "3" means a weak odor whereas "4" is moderate.

In this experience, a sample is a known blank and a second one is unknown. The other samples (profragrances and free δ-damascone) were evaluated by a blind test.

The results obtained for the different polymers are summarized in Table 2:

TABLE 2

Performance of a shampoo containing the free perfuming ingredient or the invention's polymer.

| Tested molecule | Average Intensity[1] |
| --- | --- |
| 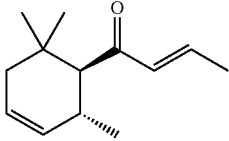 δ-damascone (reference) | 3.19 |

TABLE 2-continued

Performance of a shampoo containing the free perfuming ingredient or the invention's polymer.

| Tested molecule | Average Intensity[1] |
| --- | --- |
| 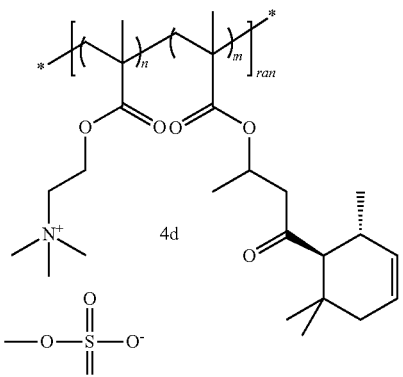 4d | 3.97 |

[1] average of the odor intensity of the dry hair one day after the washing.

The invention claimed is:
1. A perfuming composition comprising:
i) as perfuming ingredient, at least one polymethacrylate co-polymer obtainable by a process comprising the co-polymerization of at least one monomer (M) of formula

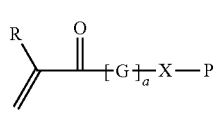
(I)

wherein a is 0;
a) P represents a radical susceptible of generating an odoriferous α,β-unsaturated ketone, aldehyde or carboxylic ester and is represented by formula

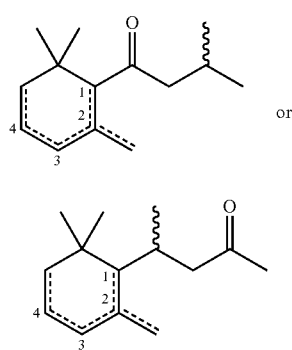

in which formula the wavy line indicates the location of the bond between said P and X and the dotted lines represent a single or double bond, $R^{10}$ indicating a methyl or ethyl group and $R^{11}$ representing a $C_6$ to $C_9$ linear or branched alkyl, alkenyl or alkadienyl group;
b) X represents an oxygen atom; and
c) R represents a methyl group; and
at least a monomer (H) of formula:

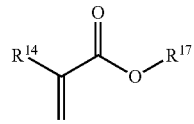
(III¹)

wherein $R^{14}$ represents a hydrogen atom or a methyl group;
$R^{17}$ represents an alkali metal atom or a hydrogen atom or a $R^{15}$
$R^{15}$ represents an acetate or propionate group, a group of formula —$(CH_2)_q$—W, or a group of formula —$(CH_2CH_2O)_x$—$CH_2(CH_2)_x$W, q representing an integer from 2 to 12, x representing an integer from 0 to 2 and W representing a functional group selected from the group consisting of COOY, $NR^{18}_2$ and $NR^{18}_3D$;
$R^{18}$ being a hydrogen atom or a methyl or ethyl group and Y being a hydrogen or an alkali metal atom, D being a monoanion, and
wherein the molar ratio between the total amount of monomer (M) and the total amount of monomer (H) is between 1/6 and 1/1;
ii) at least one ingredient selected from the group consisting of a perfumery carrier and a perfumery base; and
iii) optionally at least one perfumery adjuvant.

2. A perfumed article comprising:
i) as perfuming ingredient, at least one polymethacrylate co-polymer obtainable by a process comprising the co-polymerization of at least one monomer (M) of formula

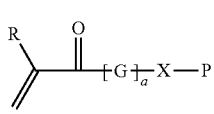
(I)

wherein a is 0;
a) P represents a radical susceptible of generating an odoriferous α,β-unsaturated ketone, aldehyde or carboxylic ester and is represented by formula

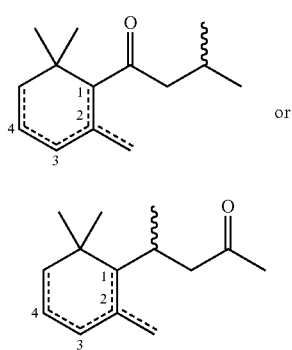

in which formula the wavy line indicates the location of the bond between said P and X and the dotted lines represent a single or double bond;
b) X represents an oxygen or a sulfur atom; and
c) R represents a methyl group; and
at least a monomer (H) of formula:

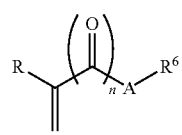
(III)

wherein, $R^{14}$ represents a hydrogen atom or a methyl group, n is 1; and
A represents an oxygen atom;
$R^6$ represents an alkali metal atom or a hydrogen atom or a $R^{15}$;
$R^{15}$ represents an acetate or propionate group, a group of formula —$(CH_2)_q$—W, or a group of formula —$(CH_2CH_2O)_x$—$CH_2(CH_2)_x$W, q representing an integer from 2 to 12, x representing an integer from 0 to 2 and W representing a functional group selected from the group consisting of COOY, $NR^{18}_2$ and $NR^{18}_3D$;
$R^{18}$ being a hydrogen atom or a methyl or ethyl group and Y being a hydrogen or an alkali metal atom, D being a monoanion, and
wherein the molar ratio between the total amount of monomer (M) and the total amount of monomer (H) is between 1/6 and 1/1; and
ii) a consumer product base.

3. A perfumed article according to claim 2, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

4. The perfuming composition of claim 1, wherein the at least one co-polymer of the perfuming ingredient is obtained by the recited process.

5. The perfumed article of claim 2, wherein the at least one co-polymer of the perfuming ingredient is obtained by the recited process.

6. The perfuming composition of claim 1, wherein $R^{14}$ is methyl.

7. The perfuming composition of claim 1, wherein the copolymer is a random copolymer of (±)-1-methyl-3-oxo-3-(trans-2,6,6-trimethyl-3-cyclohexen-1-yl)propyl 2-methacrylate and methacrylic acid; (±)-1-methyl-3-oxo-3-(trans-2,6,6-trimethyl-3-cyclohexen-1-yl)propyl 2-methacrylate and 2-(m,n-dimethylamino)ethyl methacrylate; (±)-1-methyl-3-oxo-3-(trans-2,6,6-trimethyl-3-cyclohexen-1-yl)propyl 2-methacrylate and 2-(m,n,n-trimethylamino)ethyl methacrylate sulfate; (±)-1-methyl-3-oxo-3-(trans-2,6,6-trimethyl-3-cyclohexen-1-yl)propyl 2-methacrylate and 2-(m,n-dimethylamino)ethyl methacrylate; or (±)-1-methyl-3-oxo-3-(trans-2,6,6-trimethyl-3-cyclohexen-1-yl)propyl 2-methacrylate and 2-(m,n,n-trimethylamino)ethyl methacrylate sulfate.

8. The perfumed article of claim 2, wherein $R^{14}$ is methyl.

9. The perfumed article of claim 2, wherein the copolymer is a random copolymer of (±)-1-methyl-3-oxo-3-(trans-2,6,6-trimethyl-3-cyclohexen-1-yl)propyl 2-methacrylate and methacrylic acid; (±)-1-methyl-3-oxo-3-(trans-2,6,6-trimethyl-3-cyclohexen-1-yl)propyl 2-methacrylate and 2-(m,n-dimethylamino)ethyl methacrylate; (±)-1-methyl-3-oxo-3-(trans-2,6,6-trimethyl-3-cyclohexen-1-yl)propyl 2-methacrylate and 2-(m,n,n-trimethylamino)ethyl methacrylate sulfate; (±)-1-methyl-3-oxo-3-(trans-2,6,6-trimethyl-3-cyclohexen-1-yl)propyl 2-methacrylate and 2-(m,n-dimethylamino)ethyl methacrylate; or (±)-1-methyl-3-oxo-3-(trans-2,6,6-trimethyl-3-cyclohexen-1-yl)propyl 2-methacrylate and 2-(m,n,n-trimethylamino)ethyl methacrylate sulfate.

10. The perfuming composition of claim 1, wherein P-1 or P-2 has a double bond only between carbons 3 and 4 of the ring.

11. The perfumed article of claim 1, wherein P-1 or P-2 has a double bond only between carbons 3 and 4 of the ring.

12. A method to confer, enhance, improve or modify the odor properties of a perfuming composition or of a perfumed article, which method comprises adding to said composition or article an effective amount of at least a co-polymer according to claim 1.

13. The method of claim 12, wherein P-1 or P-2 has a double bond only between carbons 3 and 4 of the ring.

14. The method of claim 12, wherein the copolymer releases, via a decomposition reaction, an αβ-unsaturated ketone, aldehyde or carboxylic ester of formula (P') derived from substituent P.

15. The method of claim 12, wherein $R^{14}$ is methyl.

16. The method of claim 12, wherein the copolymer is a random copolymer of (±)-1-methyl-3-oxo-3-(trans-2,6,6-trimethyl-3-cyclohexen-1-yl)propyl 2-methacrylate and methacrylic acid; (±)-1-methyl-3-oxo-3-(trans-2,6,6-trimethyl-3-cyclohexen-1-yl)propyl 2-methacrylate and 2-(m,n-dimethylamino)ethyl methacrylate; (±)-1-methyl-3-oxo-3-(trans-2,6,6-trimethyl-3-cyclohexen-1-yl)propyl 2-methacrylate and 2-(m,n,n-trimethylamino)ethyl methacrylate sulfate; (±)-1-methyl-3-oxo-3-(trans-2,6,6-trimethyl-3-cyclohexen-1-yl)propyl 2-methacrylate and 2-(m,n-dimethylamino)ethyl methacrylate; or (±)-1-methyl-3-oxo-3-(trans-2,6,6-trimethyl-3-cyclohexen-1-yl)propyl 2-methacrylate and 2-(m,n,n-trimethylamino)ethyl methacrylate sulfate.

* * * * *

UNITED STATES PATENT AND TRADEMARK OFFICE
CERTIFICATE OF CORRECTION

PATENT NO.      : 8,383,750 B2
APPLICATION NO. : 11/916010
DATED           : February 26, 2013
INVENTOR(S)     : Berthier et al.

It is certified that error appears in the above-identified patent and that said Letters Patent is hereby corrected as shown below:

Column 24:
Lines 35-43, delete formula (III) and insert the following:

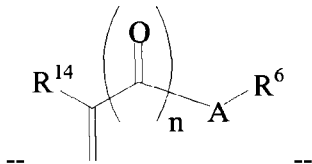

Column 25:
Line 17, delete "2-(m,n-dimethylamino)ethyl" and insert -- 2-(n,n-dimethylamino)ethyl --.
Line 19, delete "2-(m,n,n-trimethylamino)ethyl" and insert -- 2-(n,n,n-trimethylamino)ethyl --.
Line 22, delete "2-(m,n-dimethylamino)ethyl" and insert -- 2-(n,n-dimethylamino)ethyl --.
Line 24, delete "2-(m,n,n-trimethylamino)ethyl" and insert -- 2-(n,n,n-trimethylamino)ethyl --.
Line 31, delete "2-(m,n-" and insert -- 2-(n,n- --.
Line 34, delete "2-(m,n,n-trimethylamino)ethyl" and insert -- 2-(n,n,n-trimethylamino)ethyl --.
Line 36, delete "2-(m,n-" and insert -- 2-(n,n- --.

Column 26:
Line 3, delete "2-(m,n,n-trimethylamino)ethyl" and insert -- 2-(n,n,n-trimethylamino)ethyl --.
Line 26, delete "2-(m,n-" and insert -- 2-(n,n- --.
Line 29, delete "2-(m,n,n-trimethylamino)ethyl" and insert -- 2-(n,n,n-trimethylamino)ethyl --.
Line 31, delete "2-(m,n-" and insert -- 2-(n,n- --.
Line 34, delete "2-(m,n,n-trimethylamino)ethyl" and insert -- 2-(n,n,n-trimethylamino)ethyl --.

Signed and Sealed this
Ninth Day of April, 2013

Teresa Stanek Rea
*Acting Director of the United States Patent and Trademark Office*